United States Patent [19]

Rossi et al.

[11] 4,349,473
[45] Sep. 14, 1982

[54] PROCESS FOR THE PREPARATION OF ω-LACTAMS, IN PARTICULAR CAPROLACTAM

[75] Inventors: Pier P. Rossi, Garlasco; Mario Catoni, Colleferro, both of Italy

[73] Assignee: SNIA Viscosa Societa' Nazionale Industria Applicazioni Viscosa S.p.A, Milan, Italy

[21] Appl. No.: 199,218

[22] Filed: Oct. 21, 1980

[30] Foreign Application Priority Data

Nov. 2, 1979 [IT] Italy .............................. 27018 A/79

[51] Int. Cl.³ .......................................... C07D 201/10
[52] U.S. Cl. .................... 260/239.3 A; 260/326.5 FN; 546/243
[58] Field of Search .............. 260/239.3 A, 326.5 FN; 546/243

[56] References Cited

U.S. PATENT DOCUMENTS

| | | | |
|---|---|---|---|
| 3,022,291 | 2/1962 | Muench et al. | 260/239.3 A |
| 3,328,393 | 6/1967 | Ribaldone et al. | 260/239.3 A |
| 3,328,394 | 6/1967 | Ribaldone et al. | 260/239.3 A |
| 3,356,675 | 12/1967 | Muench et al. | 260/239.3 A |

*Primary Examiner*—Robert T. Bond
*Attorney, Agent, or Firm*—Wenderoth, Lind & Ponack

[57] ABSTRACT

Process for the preparation of ω-lactams (in particular caprolactam) with improved yields, by reaction of cycloaliphatic derivatives having the general formula:

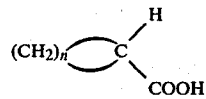

wherein $n = 3-13$ with nitrosating agents in the presence of dehydrating agents, characterized by the fact that the reaction is carried out a low temperature which is constant between stages, and in all the zones of a stage and with particular concentrations of the dehydrating agent.

7 Claims, 1 Drawing Figure

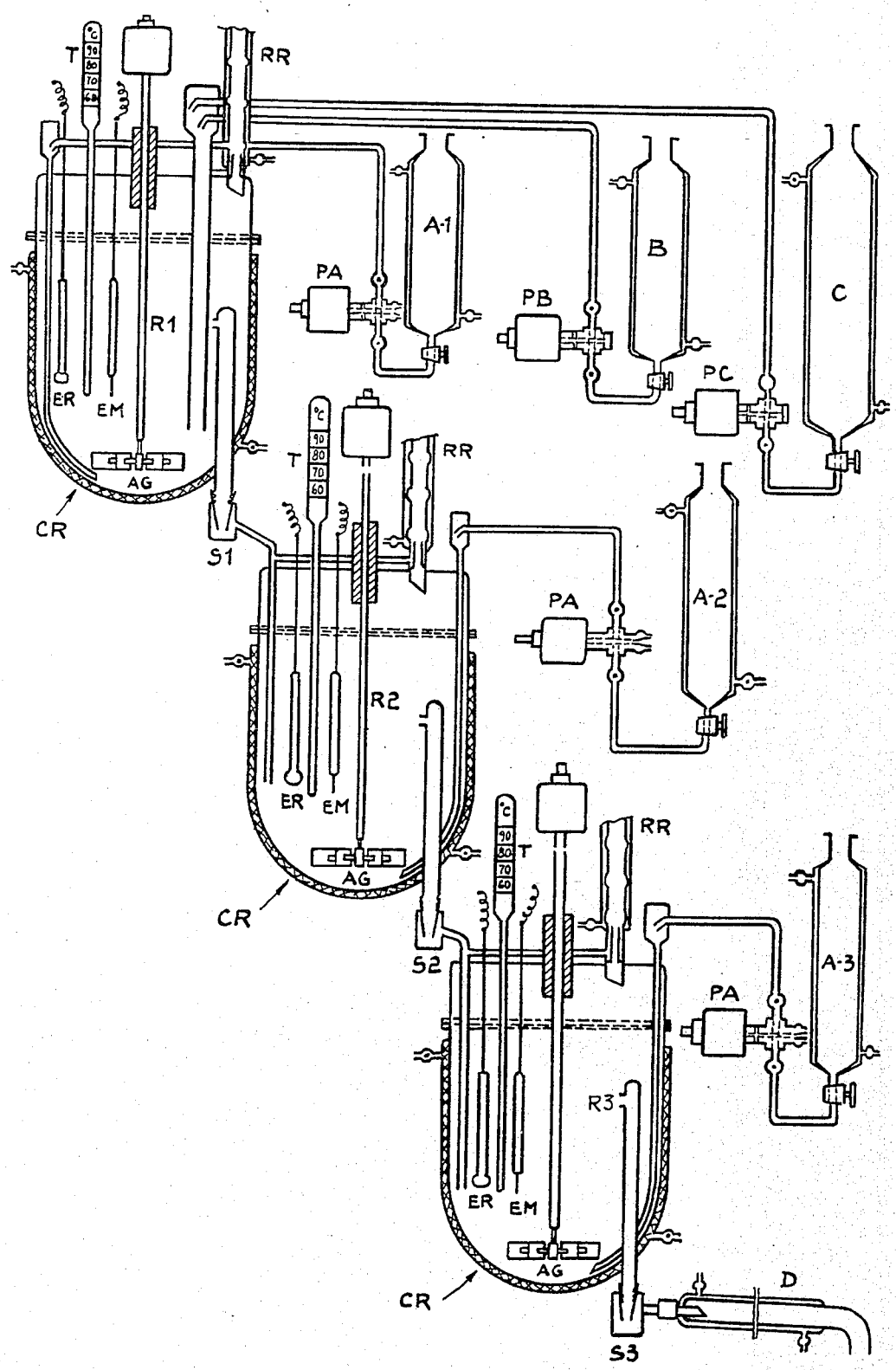

PROCESS FOR THE PREPARATION OF ω-LACTAMS, IN PARTICULAR CAPROLACTAM

BACKGROUND OF THE INVENTION

1. Field of the Invention

The present invention relates to a process for the preparation of ω-lactams, in particular caprolactam, with improved yields.

The present invention further relates to the ω-lactams thus obtained.

2. Prior Art

It is known to prepare caprolactam by reaction of cycloaliphatic compounds with nitrosating agents in the presence of a dehydrating agent. In U.S. Pat. No. 3,356,675 the preparation of caprolactam is described starting from precursors which contain the cycloaliphatic ring, in particular a cyclohexyl ring, by reaction of the same with nitrosyl acid sulphate in concentrated sulphuric acid medium and employing oleum as dehydrating agent. The reaction is carried out continuously and by stages at increasing reaction temperatures, wherein the contact times and the molecular ratios of the reagents must be predetermined.

In the aforementioned patent, the molecular ratios of the reagents, the temperature, and the reaction time, are established by preliminary tests carried out with the purpose of optimizing the process. In U.S. Pat. No. 3,356,675, when an $SO_3/NOHSO_4$ molecular ratio between 0.6 and 0.7 to 1 is maintained, a caprolactam yield of about 92–94% is obtained, the purity of the caprolactam obtained being about 98%. When oleum is employed in the reaction of the formation of caprolactam from hexahydrobenzoic acid, a part of this latter is transformed by sulphonation on the carbon in α position with respect to the carboxyl group, to form cyclohexane-1-sulphone-1-carboxylic acid, whereby the reaction yields are decreased.

It is further difficult industrially to carry out the lactamization of the cycloaliphatic compounds in stages while maintaining different temperatures from stage to stage, as taught by U.S. Pat. No. 3,356,675. Said yields of the known processes, although they are rather high, involve the formation of considerable amounts of by-products which cannot be used and have to be discharged or disposed of in a different way, at a considerable expense. Therefore it is desirable to obtain possibly quantitative yields and therefore an ecologically improved process.

SUMMARY OF THE INVENTION

The inventors have now surprisingly found, and this is one of the objects of the invention, that it is possible to increase the reaction yields by increasing the molecular ratio of the $SO_3$, or of a different dehydrating agent, to the cycloaliphatic acid, and by maintaining at the same time a low reaction temperature which is constant throughout the different stages. Since the lactamization process can be easily interrupted and therefore accumulation of nitrosyl sulphate may occur in the reactor when the temperature is decreased, which involves the possibility of violent reactions accompanied by sudden and uncontrolled or uncontrollable temperature increases which lead to the sulphonation of part of the hexahydrobenzoic acid, causing considerable losses of yield, it is very important to develop a system for the continuous and instantaneous control of the concentration of the nitrosating mixture in the reaction mass.

An object of the present invention is therefore a process for preparing omega-lactams containing from 5 to 14 carbon atoms, by reaction of cycloaliphatic acids of the general formula:

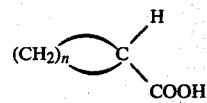

wherein $n=3-13$ and/or the corresponding anhydrides, with a nitrosating agent in the presence of dehydrating agents, characterized by the fact that the reaction is carried out at a low temperature which is maintained constant throughout the reaction stages, at a molar ratio of dehydrating agent to nitrosating agent comprised between 0.7 and 1.

The inventors have further surprisingly found, and this a further object of the invention, that it is possible to continuously control the reactivity of the system and therefore the concentration level of the nitrosating agent, by the use of redox electrodes immersed in the reaction mass. The measuring electrode is constituted by a platinum electrode, while the reference electrode is constituted by a glass electrode. The electrode system is then connected to a measuring bridge, according to known and conventional methods and systems.

The improved lactimazation reaction of cycloaliphatic compounds, which is the object of the present invention, consists therefore (when the reaction is carried out continuously in several stages, e.g. as described in U.S. Pat. No. 3,356,675), in maintaining, in all the stages, the lowest possible temperatures compatible with reaction speeds that are still industrially acceptable providing a ratio of the amount of nitrosating agent fed, to the amount used up in the reaction, such that there will not be stationary concentrations of nitrosating agents in the reactor so high as to lead to accumulations which are dangerous for the process; increasing the dehydrating agent/nitrosating acid ratio proportionally with the temperature decrease in order to improve the reaction speed; and optionally, controlling the local nitrosating mixture concentration in the reactor by the use of electrodes adapted to measure the oxidation potential of the mixture.

DETAILED DESCRIPTION OF THE PREFERRED EMBODIMENTS

The cycloaliphatic acids which may be lactimized according to the object of the invention are: hexahydrobenzoic acid, cyclododecanecarboxylic acid, or the anhydrides of the cyclohexanecarboxylic acids, etc. Hexahydrobenzoic acid, also called cyclohexanecarboxylic acid, is preferred.

As nitrosating agent, any of the agents indicated in U.S. Pat. No. 3,356,675 may be employed. As dehydrating agent there may be employed, according to the invention, $SO_3$, chlorosulphonic acid, phosphoric anhydride or even the anhydride of hexahydrobenzoic acid, the latter being suitably mixed with 100% hexahydrobenzoic acid and sulphuric acid and considering, for the purpose of calculating the molecular ratios, one mole of hexahydrobenzoic acid anhydride as equivalent to one mole of $SO_3$.

The reaction temperature may vary from 30° to 100° C. (for hexahydrobenzoic acid, preferably from 60° to 80° C.).

The reaction may be carried out in stirred reactors discontinuously, semi-continuously (viz. by charging all the reagents except the nitrosyl sulphate and adding this latter in a predetermined period of time and then discharging the reacted mass) or continuously.

A multi-stage continuous reaction is preferred for hexahydrobenzoic acid.

The thermal regulation of the reaction (which is strongly exothermic) is maintained by employing particular inert liquids in the reaction system, which liquids remove the reaction heat with their evaporation heat and maintain the reacting mixture temperature constant through their boiling temperature. Pure liquids or liquid mixtures having a boiling point equal to a temperature chosen for the reaction, may be used.

Examples of said liquids are: cyclohexane, n-hetpane, n-hexane, n-pentane, chlorinated or fluorinated hydrocarbons, nitrocompounds, etc.

When hexahydrobenzoic acid is used as cycloaliphatic acid, n-pentane, n-hexane or their mixture with cyclohexane are preferred.

In a preferred embodiment of the invention, the cyclohexyl compound and more particularly hexahydrobenzoic acid, is mixed with the oleum before carrying out the reaction with the nitrosyl acid sulphate in one of the known ways, as described e.g. in U.S. Pat. No. 3,356,675.

The reaction is carried out in several stages, conveying the nitrosyl acid sulphate to every stage in equal amounts or even in unequal amounts. For example, if there are three reaction stages, one third of the nitrosyl to the first reactor, another one third to the second reactor, and the last one-third to the last reactor, or a different subdivision may be effected, e.g. less nitrosyl sulphate may be conveyed to the first reactor and more to the others. When oleum is used in the premixed mass, the $SO_3$ may be mixed entirely with the hexahydrobenzoic acid or only a part thereof may be mixed with hexahydrobenzoic acid while the remaining part may be added to the nitrosyl sulphate. Normally the temperature regulating liquid is conveyed to the first stage of the reaction, preferably by means of a sunk pipe, below the stationary level of the reaction mass and in the vicinity of the vanes of the stirrer, or it may be coveyed to the various reaction stages.

The sulphuric solution of $NOHSO_4$ is also fed to the vicinity of the stirrer vanes. The lactam mass which overflows from one stage enters into the successive stage through a pipe provided with a syphon and a dip tube, which leads the mass into contact with the stirrer vanes. The temperature regulating liquid which is condensed, is brought back below the level of the reaction mass in the vicinity of the stirrer vanes.

In every reaction stage at least two electrodes (measuring and reference electrode) are immersed. More than one pair of electrodes may be placed in the reactor zones for which control is desired, e.g. even in the lactam mass discharge and in the passage of the same from one reactor to the following one.

EXAMPLES

Continuous multistage lactamization of hexahydrobenzoic acid, with constant temperature in all the reaction stages.

In the apparatus schematically illustrated in the drawing, consisting of three reactors in series (R1-R2-R3) each provided with a stirrer (AG), a thermometer (T), a drip refrigerator (RR), a reference electrode (ER), a measuring electrode (EM), and a heating jacket (CR), there are continuously conveyed from the doser C, 2293 g/h of previously prepared hexahydrobenzoic acid (AEB)-oleum mixture, having the following composition: 27.91% of $H_2SO_4$; 53.58% of hexahydrobenzoic acid; 11.7% of $SO_3$, the remaiing amount to 100% being constituted by by-products and reaction solvents. After about 20 min 1500 ml/h of n-hexane-cyclohexane mixture are conveyed through solvent doser B, which mixture is composed of 70% by volume of n-hexane and 30% by volume of cyclohexane, in such a way that the mixture maintains a constant temperature of 70°–72° C. in the reactor.

252 g/h of a sulphuric solution of nitrosyl acid sulphate composed of $NOHSO_4$ 68.3%; $SO_3$ 5.0%; $H_2SO_4$ 26.7% are than conveyed through the $NOHSO_4$ dosers indicated by A-1, A-2, A-3.

Water thermostatized to 72° C. is circulated in the heating jacket (CR) of the three reactors. The partially reacted mass passes from one reactor to the following one through S1, S2 and S3 and is discharged through refrigerator D.

The reaction gas prevalently composed of $CO_2$, flows out through the drip refrigerator (RR). The reagents are dosed by means of volumetric pumps PB, PC and PA; these latter are heated to avoid the crystallization of nitrosyl sulphate. After three hours of continuous work, the system is stabilized and the reagents which enter from A, B and C, are measured and weighed and the product which flows out from D is collected and weighed. The potential level corresponding to the stationary concentration of nitrosyl sulphate in the various reactors is read from time to time. During the course of the reaction carried out at 70°–72° C., the potentials, referred to the base potential of the mass at 70° C. in the absence of a reaction (considered as relative zero potential), are registered in the three reactors, and are listed in the following table as examples of data which refer to an operation lasting one hour.

| CHARGING MOLECULAR RATIOS | | | |
| --- | --- | --- | --- |
| $SO_3$ | AEB | $S_{total}$ | NO |
| 0.94 | 2.36 | 3.88 | 1 |

| DATA REGISTERED DURING AN OPERATION LASTING ONE HOUR | | | | | | | | | | |
| --- | --- | --- | --- | --- | --- | --- | --- | --- | --- | --- |
| time in min. | Acid mass g | solvent ml | $NOHSO_4$ Reactor 1 g | $NOHSO_4$ Reactor 2 g | $NOHSO_4$ Reactor 3 g | T °C. $R_1$ | T °C. $R_2$ | T °C. $R_3$ | mV $R_1$ | mV $R_2$ | mV $R_3$ |
| 0 | 0 | 0 | 0 | 0 | 0 | 71 | 72 | 73 | 160 | 70 | 60 |
| 10 | 382 | 250 | 42 | 42 | 42 | 71 | 72 | 73 | 160 | 70 | 60 |
| 20 | 764 | 500 | 85 | 84 | 84 | 71 | 72 | 73 | 160 | 70 | 60 |
| 30 | 1146 | 750 | 126 | 127 | 126 | 71 | 72 | 73 | 160 | 70 | 60 |
| 40 | 1528 | 1000 | 167 | 168 | 168 | 71 | 72 | 73 | 170 | 70 | 60 |

| DATA REGISTERED DURING AN OPERATION LASTING ONE HOUR | | | | | | | | | | | |
|---|---|---|---|---|---|---|---|---|---|---|---|
| time in min. | Acid mass g | solvent ml | NOHSO$_4$ Reactor 1 g | NOHSO$_4$ Reactor 2 g | NOHSO$_4$ Reactor 3 g | T °C. R$_1$ | T °C. R$_2$ | T °C. R$_3$ | mV R$_1$ | mV R$_2$ | mV R$_3$ |
| 50 | 1910 | 1250 | 209 | 210 | 210 | 71 | 72 | 73 | 170 | 70 | 60 |
| 60 | 2292 | 1500 | 252 | 252 | 252 | 71 | 72 | 73 | 170 | 70 | 60 |

(T = temperature; mV = milliVolt)

The operation is interrupted after 5 hours. The discharge of the lactamized mass is stratified in two phases: light and heavy phase.

28.5. g/h of pure (after titration)hexahydrobenzoic acid are analyzed out in the light phase.

448.7 g/h of pure (after titration) caprolactam (C.L.), and 677.3 g/h of pure (after titration) hexahydrobenzoic acid are analyzed and found in the heavy phase.

The reaction yields are:

| | |
|---|---|
| (Pure) hexahydrobenzoic acid fed | 1228 g/h |
| (Pure) nitrosyl acid sulphate fed | 516.3 g/h (4.0654 mols) |
| Recovered hexahydrobenzoic acid | 705.8 g/h |
| Caprolactam formed | 448.7 g/h (3.9709 mols) |

Yield of pure C.L. formed with respect to hexahydrobenzoic acid (AEB) used up:

$$\frac{1228 - 705.8}{128} = 4.0796 \text{ mols of AEB used up}$$

$$\frac{3.9709 \cdot 100}{4.0796} = 97.3\%$$

Yield of C.L. formed with respect to NOHSO$_4$ fed:

$$\frac{3.9709 \cdot 100}{4.0654} = 97.7\%$$

We claim:

1. A process for the preparation of a ω-lactam containing from 5 to 14 carbon atoms, which comprises reacting, in a plurality of stages, a cycloaliphatic acid of the formula:

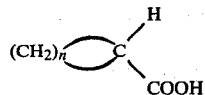

wherein n=3−13, and/or the corresponding anhydride, with a nitrosating agent in the presence of a dehydrating agent at a temperature of from 30° to 100° C. which is maintained constant throughout the plurality of the reaction stages, and at a molar ratio of the dehydrating agent/the nitrosating agent between 0.7 and 1, substantially all of the dehydrating agent being mixed with the cycloaliphatic acid and/or the corresponding anhydride prior to the reaction with the nitrosating agent, said process being carried out in a manner which prevents substantial accumulation of stationary concentrations of the nitrosating agent in the reaction mass.

2. A process according to claim 1, wherein the concentration level of the nitrosating agent is measured by the use of redox electrodes immersed in the reaction mass.

3. A process according to claim 1, wherein the dehydrating agent is SO$_3$, chlorosulphonic acid, phosphoric anhydride or a mixture of the anhydride of hexahydrobenzoic acid with 100% hexahydrobenzoic acid and sulphuric acid.

4. A process according to claim 1, 2 or 3, wherein the cycloaliphatic acid and/or corresponding anhydride is hexahydrobenzoic acid, cyclododecanecarboxylic acid, and/or the anhydride thereof.

5. A process according to claim 1, wherein hexahydrobenzoic acid is reacted with the nitrosating agent in the presence of n-pentane, n-hexane, or a mixture thereof with cyclohexane, at a temperature between 60° and 80° C.

6. A process according to claim 1, wherein hexahydrobenzoic acid is reacted with a nitrosating agent in the presence of n-hexane and cyclohexane at a temperature of about 70°–72° C.

7. A process according to claim 6, wherein the hexahydrobenzoic acid is mixed with oleum and the mixture is reacted with nitrosyl acid sulphate.

* * * * *